United States Patent [19]
Georgiou et al.

[11] Patent Number: 5,508,192
[45] Date of Patent: Apr. 16, 1996

[54] BACTERIAL HOST STRAINS FOR PRODUCING PROTEOLYTICALLY SENSITIVE POLYPEPTIDES

[75] Inventors: George Georgiou, Austin, Tex.; Francois Baneyx, Seattle, Wash.

[73] Assignee: Board of Regents, The University of Texas System, Austin, Tex.

[21] Appl. No.: 153,855

[22] Filed: Nov. 18, 1993

Related U.S. Application Data

[63] Continuation-in-part of Ser. No. 612,696, Nov. 9, 1990, Pat. No. 5,264,365.

[51] Int. Cl.$^6$ .............................. C12N 1/20; C12N 15/01
[52] U.S. Cl. .................. 435/252.8; 435/69.1; 435/172.3
[58] Field of Search ............................. 435/252.8, 252.3, 435/69.1, 71.2, 172.3

[56] References Cited

U.S. PATENT DOCUMENTS

| | | | |
|---|---|---|---|
| 4,656,131 | 4/1987 | Kitano et al. | 435/68 |
| 4,948,729 | 8/1990 | Piatak, Jr. et al. | |
| 5,143,846 | 9/1992 | Huala et al. | 435/252.33 |
| 5,264,365 | 11/1993 | Georgiou et al. | 435/252.8 |

FOREIGN PATENT DOCUMENTS

| | | |
|---|---|---|
| WO88/05821 | 8/1988 | WIPO . |
| WO89/02465 | 3/1989 | WIPO . |

OTHER PUBLICATIONS

Strauws et al., *Genes & Development*, 2 (12B) 1851–1858 (1988).
Baneyx, F. and Georgiou, G., *Journal of Bacteriology*, 172 (1):491–494 (Jan. 1990).
Swany, K. H. S. and Goldberg, A. L., "Subcellular Distribution of Various Proteases in *Eschercia coli*", *J. of Bacter.*, 149(3):1027–1033 (Mar. 1982).
Strauch, K. L. and Beckwith, J., *Proc. Natl. Acad. Sci. USA*, 85:1576–1580 (Mar. 1988).
Cheng, et al., *Journal of Bacteriology*, 140(1):125–130 (Oct. 1979).
Dialog Search Report Abstracts, Jul. 25, 1990, Items 1–171.
Elish, et al., "Biochemical Analysis of Spontaneous *fepA* Mutants of *Eschercia coli*", J. Gen. Microbiology, 134:1355–1364 (1988).
McIntosh, et al., *Journal of Bacteriology*, 137(1):653–657 (Jan. 1979).
Chaudhury, A. M. and Smith, G. R., "*Eschercia coli* recBC Deletion Mutants", J. of Bacteriology, 160(2):788–791 (Nov. 1984).
Russell, et al., *Journal of Bacteriology*, 171(5):2609–2613 (May 1989).
Dykstra, et al., *Journal of Bacteriology*, 157(1):21–27 (Jan. 1984).
Pacaud, Michèle, *The Journal of Biological Chemistry*, 257(8):4333–4339 (Apr. 1982).
Palmer, S. M. and St. John, A. C., *Journal of Bacteriology*, 169(4):1474–1479 (Apr. 1987).
Strauch, et al., *Journal of Bacteriology*, 171(5):2689–2696 (May 1989).
Lazdunski, A. M., "Peptides and proteases of *Escherichia coli* and *Salmonella typhimurium*", *FEMS Microbiology Reviews*, 63:265–276 (1989).
Baneyx, F. and Georgious, G., *Enzyme Microb. Technol.*, 11:559–567 (Sep. 1989).
Georgiou, et al., *Biotechnology and Bioengineering*, 32:741–748 (1988).
Herschko, Avram and Ciechanover, Aaron, "Mechanisms of Intracelular Protein Breakdown", *Ann. Rev. Biochem.*, 51:335–364 (1982).
Huse, et al., *Science*, 246:1275–1281 (Dec. 1989).
Goldberg, A. L. and St. John, A. C., *Ann. Rev. Biochem.*, 45:747–803 (1976).
Weichenhan, D. and Wachkernagel, W., *Molecular Microbiology*, 3(12):1777–1784 (1989).
Georgiou, G., "Optimizing the Production of Recombinant Proteins in Microorganisms", *AIChE Journal*, 34(8):1233–1248 (Aug. 1988).
Smith, et al., *The Journal of Biological Chemistry*, 246(10):3320–3329 (May 1971).
Nossal, N. G. and Heppel, L. A., *The Journal of Biological Chemistry*, 241(13):3055–3062 (Jul. 1966).
Laemmli, U. K., *Nature* (London), 227:680–685 (1970).
Chang, A. C. and Cohen, S. N., *Journal of Bacteriology*, 134(3):1141–1156 (Jun. 1978).
Maniatis, et al., in *Molecular Cloning: A Laboratory Manual*, Cold Spring Harbor, N.Y., Cold Spring Harbor Laboratory Press (1982).
Ausubel, et al., in *Current Protocols in Molecular Biology*, John Wiley & Sons, New York, N.Y. (1987).
Miller, C. G. in *Escherichia coli* and *Salmonella typhimurium: Cellular and Molecular Biology*, vol. 1, F. C. Neidhardt, Ed., American Society for Microbiology, Washington, D.C., 680–691 (1987).
Dykstra, C. C. and Kushner, S. R., "Physical Characterization of the Cloned Protease III Gene from *Escherichia coli* K–12*", *Journal of Bacteriology*, 163(3):1055–1059 (Sep. 1985).
Grodberg, J. and Dunn, J. J., "ompT Encodes the *Escherichia coli* Outer Membrane Protease That Cleaves T7 RNA Polymerase during Purification", *Journal of Bacteriology*, 170(3):1245–1253 (Mar. 1988).
Baneyx, F. and Georgiou, G., "Construction and Characterization of *Escherichia coli* Strains Deficient in Multiple Secreted Proteases: Protease III Degrades High Molecular--Weight Substrates In Vivo", *Journal of Bacteriology*, 173(8):2696–2703 (Apr. 1991).

*Primary Examiner*—Mindy B. Fleisher
*Assistant Examiner*—Nancy T. Vogel
*Attorney, Agent, or Firm*—Arnold, White & Durkee

[57] ABSTRACT

The invention relates to methods of producing recombinant polypeptides in protease-deficient bacterial hosts. Constructs of single, double, triple and quadruple protease deficient and protease/rpoH mutants of *E. coli* are described. Proteolytically sensitive polypeptides may be expressed and secreted in such cells, providing significantly increased yields compared with expression in wild-type strains.

7 Claims, 5 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: nucleotide ( v i ) ORIGINAL SOURCE: Plasmid ( x i ) SEQUENCE DESCRIPTION: SEQ ID NO:1:

```
GGA CCA GGA ATT CCG GGT CAC CCA                           24
Gly Pro Gly Ile Pro Gly His Pro
```

( 2 ) INFORMATION FOR SEQ ID NO:2:

( i ) SEQUENCE CHARACTERISTICS:
        ( A ) LENGTH: 8 amino acid residues
        ( B ) TYPE: amino acid
        ( C ) STRANDEDNESS: single
        ( D ) TOPOLOGY: linear ( i i ) MOLECULE TYPE: Peptide ( v i ) ORIGINAL SOURCE: Bacteria ( x i ) SEQUENCE DESCRIPTION: SEQ ID NO:2:

```
Gly Pro Gly Ile Pro Gly His Pro
 1               5
```

BACTERIAL HOST STRAINS FOR PRODUCING PROTEOLYTICALLY SENSITIVE POLYPEPTIDES

The United States Government has rights in the present invention pursuant to the terms of Grant No. CBT-8657471 awarded by the National Science Foundation.

This is a continuation-in-part of Ser. No. 07/612,696, filed Nov. 9, 1990, now U.S. Pat. No. 5,264,365 (Nov. 23, 1993), the entire disclosure of which is herein incorporated by reference without disclaimer.

BACKGROUND OF THE INVENTION

1. Field of the Invention

The invention relates generally to recombinant DNA technology methods employing novel protease and heat shock protein deficient bacteria for the expression of polypeptides. Significantly improved yields of protease sensitive polypeptide products are obtainable employing the disclosed methods. Several novel protease-deficient mutants are disclosed, including a ptr mutant lacking Protease III and mutants with degP and rpoH deficiencies.

2. Description of Related Art

The expression of proteins in bacteria is by far the most widely used approach for the production of cloned gene products, many of which have important medical and commercial application. It is common to first obtain a polypeptide encoded by a cloned or mutated gene in *E. coli*, a readily available and well-characterized bacterial host cell. However, for various reasons, expressed bacterial polypeptide products may not be active. In some cases this may be due to incorrect folding or failure of essential post-translation modification in the host cell. Additionally, yields and/or recovery of the polypeptide product may be low. Alternate expression systems are therefore desirable to overcome these problems.

Bacterial cells are generally preferred for protein/polypeptide expression for several reasons. As a rule, prokaryotic cells are easier to grow than eukaryotic cells such as human cell lines. Additionally, a wealth of sophisticated molecular genetic tools and thousands of mutants with useful phenotypes are available to manipulate for particular expression problems.

The expression of proteins in bacteria benefits from the availability of a range of strong promoters capable of directing high levels of transcription of the desired heterologous gene. Translation of the mRNA is optimized by using a strong ribosome binding site (RBS) and substituting with the appropriate codons at the 3' of the gene. Such manipulations are routine and can result in very high rates of protein accumulation, often exceeding 50% of the total cell protein, provided that the protein is stable in vivo and is not susceptible to proteolytic degradation.

The expression of heterologous proteins in a form that is excreted from the bacteria into the extracellular fluid offers important technological advantages. First, once a protein has been exported from the cytoplasm, it becomes exposed to an oxidative environment which favors the formation of disulfide bonds, an important step in the correct folding of the polypeptide chain. In contrast, disulfide bond formation does not occur within the cytoplasm. Second, exported proteins are first synthesized with an N-terminal extension called the leader peptide which is precisely excised from the protein concomitant with transport through the membrane. As a result, export from the cytoplasm is an effective way of ensuring that the protein contains the correct N-terminal amino acid. On the other hand, proteins expressed in the cytoplasm often contain an additional methionine amino acid at their N-terminus. The presence of the additional N-terminal methionine is highly undesirable in pharmaceutical proteins where it is imperative that the protein sequence produced in bacteria is identical to the sequence of the corresponding protein in nature. Finally, it is desirable to express proteins in secreted form because of ease in separation from other cellular components.

A number of useful eukaryotic proteins have been cloned and expressed in bacterial cells, including human insulin and proinsulin, human and bovine somatotropins, interferons and tissue plasminogen activator. Recently, Huse and coworkers (1989) constructed a bacteriophage lambda system which allows the expression and rapid screening of mouse $F_{ab}$ antibody fragments in *E. coli*.

*Escherichia coli* has been the most widely used microorganism for the production of commercially important recombinant proteins. Despite the lack of certain kinds of post-translational processing and the production of endotoxins, *E. coli* presents numerous advantages for protein expression. Its genetics are well understood, it can be grown to high densities on inexpensive substrates, and fermentation scale-up is straightforward (Georgiou, 1988).

However, one of the major problems associated with the expression of heterologous polypeptides in *Escherichia coli* and related bacteria is the degradation of cloned gene products by host-specific proteases (Baneyx and Georgiou, 1992). In a manner similar to that occurring in eukaryotic cells, energy-dependent processes are important for the degradation of *E. coli* proteins with abnormal conformations (Goldberg and St. John, 1976; Hershko and Ciechanover, 1982). Most *E. coli* proteases hydrolyze peptide bonds via an energy-independent pathway. At least 25 proteases and peptidases have been identified in different cellular compartments of *E. coli* (Lazdunski, 1989; Miller, 1987). The biochemical characterization of these enzymes is incomplete and there is relatively little information on their physiological role. One or more of these proteases may act upon any given polypeptide to effect degradation and thereby reduce yields, sometimes quite drastically.

One approach to solving the problem of low polypeptide production in bacterial host cells has been the use of an inducible expression system in combination with a constitutively protease-deficient bacterial host strain. This method increases polypeptide yields only if the expressed polypeptide is a substrate for the deficient protease. For example, production of an immunologically functional antibody fragment in a constitutively lon⁻ and/or htpR⁻ *E. coli* strain has produced low yields (Field, et al., 1989) even though such strains are protease deficient.

Several strains of *E. coli* deficient in proteases or genes controlling the regulation of proteases are known (Beckwith and Strauch, 1988; Chaudhury and Smith, 1984; Elish, et al., 1988; Baneyx and Georgiou, 1992). Some of these strains have been used in attempts to efficiently produce proteolytically sensitive polypeptides, particularly those of potential medical or other commercial interest. However, while increased yields of some expressed proteins have been improved, problems of relatively low yield and/or poor growth of the host cell continue to persist.

Singly protease-deficient mutants of *Escherichia coli* have been reported. These include genetically engineered strains deficient in degP and a spontaneous mutant, UT4400, which lacks the entire ompT gene together with a sizable piece of adjacent DNA (McIntosh, et al., 1979). Mutants carrying large deletions in the ptr gene have been isolated (Chaudhury and Smith, 1984). However, in those bacteria all or at least part of the adjacent genes recC, recB and recD is missing. Such bacteria tend to be unstable and generally exhibit growth defects and low protein production. The recC, recB and recD genes are known to be important for cell viability and stable propagation of plasmids in bacteria such as E. coli. Significant portions of these adjacent genes appear to be missing in the reported ptr deficient mutants.

A ptr mutant strain has also been isolated after chemical mutagenesis (Cheng and Zipster, 1979). Cheng et al. exposed an E. coli culture to the mutagen nitrosoguanidine and by brute force screening isolated three mutants that exhibited decreased rates of degradation of the "auto α" fragment of β-galactosidase which is a substrate for protease III. In vitro, the three point mutants isolated by Cheng et al., exhibited about 5% of the activity detected in wild type strains. However, the three mutants did not affect the degradation of several β-galactosidase nonsense mutants in vivo. This finding led Cheng et al. to conclude that the activity of protease III in vivo in these mutants was probably not affected. If the activity of protease III in vivo is unaffected by the mutations then, obviously, these strains are not suitable for protein expression. Furthermore, Cheng et al. did not investigate whether the mutations they isolated have any deleterious effects on cell growth and plasmid stability.

As found in later studies (e.g., Claverie-Martin et al. 1987), the ptr gene which encodes protease III overlaps the recC genes which encode two exonuclease V subunits. Exonuclease V is an important enzyme for DNA repair, resistance to UV irradiation and the stable maintenance of expression vectors in the cell (Baneyx and Georgiou 1991). Randomly generated mutations in the ptr gene are expected to interfere with the expression of the overlapping recB and recC genes. Mutations that affect the expression of the RecB and RecC subunits of exonuclease V can impair cell viability and substantially decrease the expression of heterologous proteins.

Other singly protease deficient mutants have been produced. Using a genetic engineering approach, Escherichia coli has been mutagenized to produce a cell with a defective periplasmic protease (Beckwith and Strauch, 1988). A degP deletion mutant was constructed and recombined into an E. coli chromosome (Strauch and Beckwith, 1988). Protein A-β-lactamase, a proteolytically sensitive protein, is stabilized three-fold in such a degP mutant (Baneyx and Georgiou, 1989; Baneyx and Georgiou, 1990).

Hara et al. (1991) have isolated transposition mutations that disable another secreted protease, Prc. This protease was first isolated on the basis of its ability to cleave the periplasmic protein Penicillin-Binding Protein 3. Subsequently, it was also identified as a protease that selectively degrades proteins with a non-polar C-terminus and was renamed Tsp (Silber et al. 1992). Prc(tsp) mutant strains exhibit certain abnormal growth characteristics such as inability to form colonies at elevated temperatures when grown in LB media without salt. Additionally, they leak periplasmic enzymes into the growth medium and grow as elongated filaments. Hara et al. (1991) and Silber et al. (1992) did not investigate whether prc(tsp) mutants increase the stability of recombinant secreted proteins or whether they impair cell viability when combined with other loci that impair protein turnover in the cell envelope.

Most proteins are degraded by more than one protease. Therefore, use of mutants deficient in the synthesis of a single enzyme may only partially prevent the degradation of the product. Inactivation of multiple proteolytic enzymes may lead to higher production. The challenge is complex because there is no assurance that disablement or deletion of any given protease or combination of proteases will result in a viable host cell. Additionally, even where singly protease-deficient microorganisms are available, growth and/or viability is typically affected so that yields of overexpressed polypeptide products are low, making such microorganisms of little commercial value.

Heat shock proteins are among the proteolytic enzymes involved in protein catabolism in the cytoplasm. Heat shock protein synthesis is induced by growth at elevated temperatures or by exposure to stressful conditions such as ethanol. Heat shock results in the overproduction of heat shock proteins and is accompanied by increased degradation of puromycyl polypeptide fragment (Strauss et al. 1988). In turn, the accumulation of abnormal polypeptides, resulting from treatment with puromycin, incorporation of canavanine or overproduction of foreign proteins, causes induction of the heat shock response (Goff and Goldberg 1985).

Transcription of the heat shock regulon is controlled by the RNA polymerase sigma factor, $\sigma^{32}$. The effect of $\sigma^{32}$ mutations on the expression of secreted proteins is not known. There are no secreted proteases whose synthesis is dependent on $\sigma^{32}$.

There is therefore a need to provide microorganisms that show good viability, stability and, importantly, are suitable hosts for expression of proteolytically sensitive polypeptides.

SUMMARY OF THE INVENTION

The present invention addresses one or more of the foregoing problems by providing methods of producing high yields of recombinant proteins in genetically engineered bacterial hosts. The new methods employ unique protease-deficient and heat shock protein-deficient bacteria constructed to contain deficiencies in one or more protease and/or heat shock protein encoding genes. These bacteria may be transformed with a cloning vector which includes a DNA sequence encoding a desired polypeptide and cultured under conditions permitting expression of that polypeptide. A suitable mutant bacterium is selected from a group which includes single, double, triple and quadruple protease-deficient bacteria, single-protease deficient bacteria which also carry a mutation in the rpoH gene, and double, triple or quadruple protease deficient bacteria carrying a mutated rpoH gene.

A general object of the invention is to employ the disclosed mutant bacteria to produce proteolytically sensitive polypeptides. Preferred mutant bacterial hosts include ptr deficient, ompT, degP, ptr, prc deficient, ompT, degP, ptr deficiencies combined with rpoH mutations, and ompT, degP, ptr, prc deficiencies combined with rpoH mutations. The ompT, degP, ptr and prc deficiencies are chromosomal deletions while the rpoH mutations are chromosomal alterations such as point mutations.

A singly protease deficient bacterium useful for practice of the invention is a recombinant bacterium which lacks the ptr gene. This gene encodes Protease III; thus, polypeptides expressed in bacterial cells lacking Protease III will not be subject to proteolysis by that enzyme. An important characteristic of the recombinant bacterium is the substantially normal expression of the polypeptide product of genes recB, recC and recD. The host cell therefore retains exonuclease V activity which is considered important in allowing the cell to maintain normal viability and growth characteristics as well as stable maintenance of transformed plasmid expression vectors. Other ptr deficient mutants have been reported; however, these display poor growth and viability characteristics, apparently because of deletion of portions of recB, recC and recD genes which are adjacent to the ptr gene. In contrast, the ptr deficient bacterium of the present invention has excellent growth characteristics and is genetically stable (i.e., phenotype is stable).

One may employ the genetically engineered bacteria of the present invention which are deficient in the polypeptide gene products of degP, ompT, ptr or prc or in combination with mutations in rpoH to express polypeptides, particularly being useful for the expression of polypeptides sensitive to one or more of the bacterial cell proteases. For example, scF$_v$ antibody is typically expressed in very small amounts in $E.$ $coli$. Triply protease deficient bacteria such as the degP, ompT, ptr mutants provide good yields of such protease-sensitive polypeptides, including fusion polypeptides such as protein A-β-lactamase and MalE-scF$_v$ fusions. Other proteolytically sensitive polypeptides include proinsulin, phosphatase, immunoglobulin F$_v$ fragments, epidermal growth factor, interleukin, interferon, somatotropin, insulin-like growth factors, and fusions of single chain antibody fragments to binding proteins.

The combination of a degP chromosomal deficiency with an rpoH mutation reduces the activity of $\sigma^{32}$, thereby allowing enhanced production of secreted polypeptides. This was surprising because the rpoH regulon is not known to affect either secreted proteases or other genes that might be involved in proteolysis in the periplasmic space. Furthermore, the degree of enhancement of protein production is substantially higher than obtained in either single degP or single rpoH mutants. Single rpoH mutants increase the synthesis of certain proteins such as Protein A-β-lactamase, but for other secreted proteins, e.g., alkaline phosphatase fusions, rpoH mutations are often destabilizing. This is because the expression of such proteins in rpoH mutants results in increased synthesis of the protease DegP which in turn causes more degradation. Thus the beneficial effect of rpoH mutations occurs primarily in strains that are also deficient in DegP.

In general, the mutant microorganisms of the invention are constructed from prokaryotes, usually gram-negative bacteria and preferably those with genetic makeup similar to the $E.$ $coli$ or Salmonella strains. It is known, for example, that the degP and ompT gene sequences in $E.$ $coli$ are homologous to those of Salmonella. (Johnson et al., 1991; Sodeinde and Goguen, 1989). In addition to Salmonella strains, other strains such as $Erwina$ $carotavora$, $Neisseria$ $gonorrhoeae$, $Pseudomonas$ $aeruginosa$ and $Klebsiella$ $pneumoniae$ may be useful. It is contemplated that different strains or other mutations of $E.$ $coli$ or Salmonella will be suitable for practicing the disclosed methods of producing recombinant polypeptides. Such other bacteria are expected to be amenable to genetic manipulation similar in principle to the examples illustrated with $E.$ $coli.$ One will generally wish to select a mutant bacterial strain encoding at least two secreted proteases from at least two genes. The mutants constructed from these strains will be suitable hosts for transformation with a variety of expression vectors resulting in the production of various proteins. The proteins produced are not native to the mutant host; that is, these proteins are heterologous. Homologous proteins are native to the host.

The invention also includes methods for preparing recombinant polypeptides using the novel mutant microorganisms.

A protease deficient mutant, preferably constructed from $E.$ $coli$ or Salmonella, is transformed with an expression vector suitable for expression of a selected polypeptide. Appropriate expression vectors are well known and readily constructed or purchased. For example, expression vector pFB3 is capable of expressing a protein A-β-lactamase fusion protein. Other vectors suitable for expression of a secreted polypeptide product in $E.$ $coli$ include the pIN-III-OmpA vector in which the desired polypeptide is expressed as a fusion protein to the OmpA leader peptide and transcribed from an lpp-lac promoter (Ghrayel and Inouye, 1984); pMAL expression vectors used to construct secreted fusion proteins to the Maltose Binding protein, Male (New England Biolabs, Beverly, Mass.) for simplified purification; and pZZ18 which allows expression of a desired polypeptide as a fusion to an IgG binding domain from $S.$ $aureus$ Protein A (Pharmacia, Inc., Biscataway, N.J.).

Vectors may be selected or specifically designed for expression of particular proteins or polypeptides; for example, proinsulin, phosphatase, immunoglobulin F$_v$ fragments, epidermal growth factor, interleukin, interferon, somatotropin and insulin-like growth factors. Different proteins will vary in susceptibility to the different proteases normally produced by the host cell. One will therefore select an appropriate protease deficient host for the particular polypeptide desired. The transformed host is then incubated in a suitable medium from which the expressed protein may be recovered.

In most instances where low yields of polypeptides are obtained in wild-type host cells, it will be desirable to use a multiple protease-deficient mutant rather than a single protease-deficient bacterium. This is generally the case when a polypeptide chain contains cleavage sites that are recognized by different proteases. In these instances, increased stability to proteolytic degradation will be obtained in bacterial strains lacking proteases that attack those cleavage sites. The benefit obtained by using multiply protease deficient strains depends on the polypeptide expressed. Inactivation of multiple proteases in conjunction with the presence of other mutations that may be desirable for expression may result in lower growth rates and in some cases increased susceptibility to cell lysis, particularly in large scale, high density fermentation. As illustrated in the Examples, the expression of Protein A-β-lactamase is increased in the triply protease deficient mutant SF130 (deficient in OmpT, DegP and Protease III).

A significant increase in expression was also observed in strains SF210 and SF310 which are deficient in DegP and carry a mutation in the rpoH gene which reduces the expression of heat shock proteins. However, when a quadruple mutant with the genotype degP, ptr, ompT, rpoH15 was constructed by P1 transduction it was found that the cells grew slowly, reverted to the rpoH$^+$ phenotype at high frequency and, rather unexpectedly, expression of protein A-β-lactamase was lower than observed in the triply protease deficient strains or in the degP, rpoH15 double mutant. One will therefore wish to select a mutant best suited for expression of the desired polypeptide. This will require some experimentation to select the best system. For some applications, even where growth of the host cell is slow, it is contemplated that mutants such as degP, ompT, ptr, rpoH will be optimal for production of unusually senstive polypeptides.

The invention is particularly suitable for producing proteolytically sensitive fusion proteins such as protein A-β-lactamase. β-lactamase is a small monomeric protein involved in the hydrolysis of the β-lactam ring of many antibiotics such as penicillin, nitrocefin and cephaloridine while protein A binds with high affinity to the $F_c$ fragment of IgG antibodies. The fusion protein, expressed by the plasmid vector pFB3, is secreted into the periplasmic space of *E. coli* cells, where it assumes a fully bifunctional conformation, i.e., it displays IgG binding ability and penicillinase enzymatic activity comparable to those of the authentic protein A and β-lactamase, respectively. However, although both protein A and β-lactamase are stable under normal conditions when expressed separately in *E. coli*, the fusion protein is highly susceptible to proteolytic degradation. Most of the degradation occurs within the lactamase domain of the hybrid protein (Baneyx and Georgiou, 1989). Therefore, the amount of penicillinase activity (e.g., β-lactamase activity against benzylpenicillin) present in cells harboring the plasmid vector expressing the fusion protein is directly proportional to the amount of intact protein A-β-lactamase. This property makes protein A-β-lactamase a suitable substrate for developing methods to reduce proteolysis in *E. coli*.

Expression of proteolytically sensitive polypeptides in the mutant microorganisms may be controlled to some extent by the medium in which they are grown and some of the components added to the medium. The mutant microorganisms described, all of which contain expression vectors, grow well in complex and in minimal media, for example, LB medium or M9 medium.

The inventors contemplate the construction of mutant organisms having deficiencies in more than four proteases. Many gram-negative bacteria express at least seven or eight different proteases that degrade secreted polypeptides. Thus, once the appropriate genes have been cloned and the gene products are known, one could select deletions or other mutations for these singly protease-deficient organisms and propagate such mutations in other strains already containing deletions or mutations in proteolytic activities. However, since viability and growth of the genetically constructed engineered organism may be of major concern, care must be taken to avoid the accidental deletion or mutagenesis of genes involved in cell viability, plasmid stability or other essential cellular processes and located in the vicinity of genes encoding proteolytic activities.

The methods disclosed for the construction of double and triple protease-deficient mutant microorganisms are contemplated as applicable to the construction of other multiply protease-deficient microorganisms. Generally, one will isolate a mutant protease gene and recombine it into the chromosome. The mutated gene will be transferred into another protease deficient strain. The multiple protease-deficient mutant generated may then be employed for the inactivation of additional proteases by repeating this procedure. Several proteases other than Protease III, OmpT, DegP and Tsp(Prc0,) are known in *E. coli;* for example, Protease I, Protease Mi, Protease V or Protease VI. Once the gene sequence for any protease is known, it may be cloned and amplified, subjected to mutagenesis and then used to transform other cells. The procedure may be repeated to produce higher multiplicities of protease deficiencies.

It is expected that the deactivation of a large number of proteolytic enzymes at some point will compromise the cell's viability. For this reason it is likely that a set of strains deficient in different combinations of up to four proteases will allow flexibility in selecting a mutant host most appropriate for expression of a desired polypeptide without unduly compromising the cell's efficiency because of poor growth. Strains containing defects in the subset of proteolytic enzymes that act on a particular protease sensitive polypeptide thus provide the highest possible production without compromising the cell's viability, protein synthetic capacity or genetic stability. Further, optimal growth conditions for each mutant will have to be determined as there may be some variations in medium, pH and trace element addition such as $Zn^{+2}$ supplementation.

DETAILED DESCRIPTION OF PREFERRED EMBODIMENTS

Figure 1:
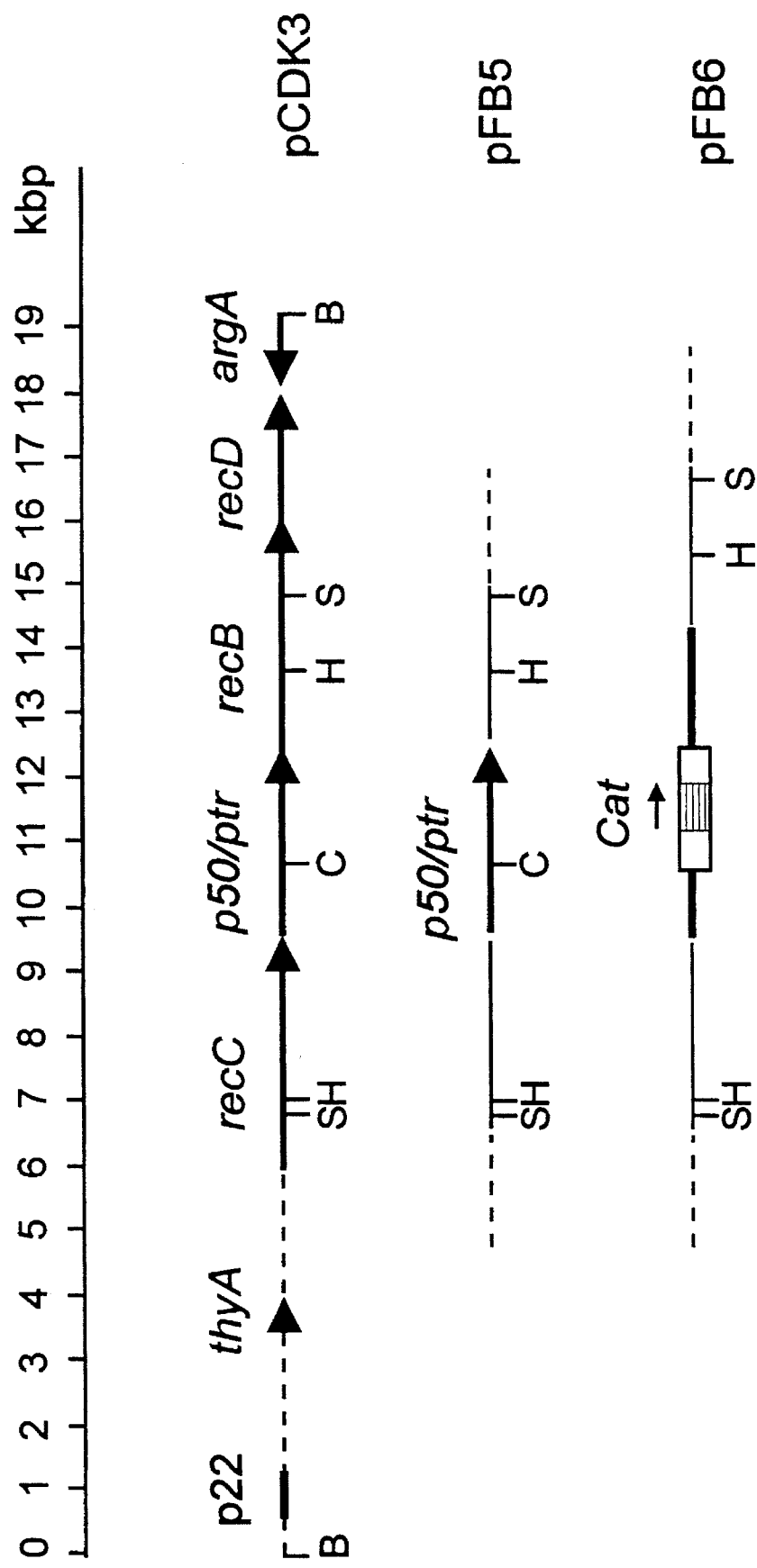
FIG. 1 shows the construction of the ptr32::Cat' mutation. Only the relevant portions of the plasmid are shown. Restriction site abbreviations are: B, BamH I; Ca, ClaI; H, Hind III; and S, Sal I.

The invention concerns new methods of producing significantly improved yields of polypeptides in host cells by employing single, double, triple or quadruple protease deficient bacterial cells. The invention also concerns host cells deficient not only in secreted proteases but further having an rpoH gene with reduced $\sigma^{32}$ activity.

*E. coli* SF 120 (ATCC Accession Number 55099) has a deficiency in proteases OmpT, DegP and Protease III. Deficiency in each of these proteases is caused by a mutation in the respective genes coding for these proteases. These genes are ompT, degP and ptr. The mutations may be either complete or partial deletions. Among the genetically engineered bacteria employed in the methods of the present invention is a triple protease-deficient mutant microorganism constructed by transferring a ptr mutation from one strain into another mutant organism having ompT and degP deletions.

An ompT, degP and ptr deficient bacterial cell was constructed from a single protease deficient strain. Mutant strain UT4400 is a spontaneous mutant in which the entire ompT gene together with a sizable piece of adjacent DNA has been deleted from the chromosome. P1 transduction was employed to transfer chromosomal DNA from the ompT mutant into degP mutant KS474. A triple protease-deficient mutant strain was then constructed by generalized P1 transduction transfer of the ptr gene mutation from an appropriate strain into double ompT degP mutants.

The triple mutant, *E. coli* KS474, was then employed to express protein A-β-lactamase. An enhancement of stability of the fusion protein was observed compared with expression from the wild type bacterium and, surprisingly, significant enhancement when compared with expression in the doubly protease-deficient mutant degP ompT or the single protease deficient mutants, ompT or degP. This suggested that, in general, the greater the number of proteases lacking in the mutant organism, the higher the yield of product.

It is contemplated that ptr degP ompT mutants may also be constructed by transferring a ptr mutation into any genetic background deficient in DegP and OmpT proteolytic activities by using P1 transduction or similar techniques. Alternatively, such mutants may be constructed by transferring an ompT mutation into any genetic background deficient in Protease III and DegP or by transferring a degP mutation in any genetic background deficient in Protease III and OmpT by using P1 transduction or similar techniques. A particular embodiment of this mutant organism is the *E. coli* stain SF120 (ATCC Accession No. 55099). The OmpT DegP and Protease III deficiencies characteristic of the mutant organisms that are triply protease-deficient may be characterized in different ways depending on the nature of the mutation in the respective genes which code for these proteases. For example, the mutations in the genes coding for these proteases may be due to deletions and such deletions result in no product of the proteins that exhibit the proteolytic activity ascribed to DegP, OmpT and Protease III. However, not all mutations are deletions and similar results can be obtained with other mutations including point, missense, nonsense and frameshift mutations, mutations resulting from site specific mutagenesis or other mutagenesis techniques. In certain cases, mutations in portions of the genes encoding the proteases may be such that a gene product is expressed but there is a substantial loss or even lack of proteolytic activity. Mutations in any one or more of the three genes may also result in either lack of gene product or products having substantially lowered activity.

The single Protease III deficient genetically engineered bacterium previously discussed is derived from a gram-negative bacterium which encodes Protease III. This mutant expresses an active polypeptide product of genes recC, recB and recD which are adjacent to the ptr gene in the chromosome but is deficient in the ptr gene product, Protease III. Proteolytically sensitive proteins that may be produced by the mutant organism are not significantly degraded because of the deficiency in Protease III. The polypeptide product expressed by genes recC, recB and recD exhibits exonuclease V activity. The expression of this activity is important for the viability of the organism and the stable propagation of expression vectors. Other reported ptr mutants appear to contain mutations involving deletions of both the ptr gene and genes recC, recB and recD and hence, thereby lacking exonuclease V activity (Chaudhury and Smith, 1984), resulting in a mutant microorganism that has poor growth characteristics and genetic instability. In contrast, the engineered mutant constructed as part of the present invention exhibits normal exonuclease V activity but lacks Protease III activity.

The degP ompT mutant organism is deficient in proteases DegP and OmpT due to a partial deletion of gene degP and a total deletion of ompT. This is not to say that the same result could not be achieved with other mutations of either gene resulting in each protease either lacking significant activity or not produced by the gene. OmpT degP mutants can be prepared by transferring an ompT mutation into any genetic background containing a degP mutation using P1 transduction. Alternatively, ompT degP mutants may be obtained by introducing a degP mutation into any genetic background containing an ompT mutation by using P1 transduction or a similar technique. Any ompT ptr or degP ptr mutant may be prepared by standard methods of P1 transduction to transfer a ptr mutation into an appropriate strain, usually *E. coli* containing a degP or ompT mutation. Alternatively, ompT ptr (or degP ptr) mutants can be constructed by transferring an ompT (or degP) mutation into any genetic background deficient in Protease III using P1 transduction. When these mutant strains are transformed with an appropriate expression vector, the proteolytically sensitive proteins expressed are recovered substantially intact, that is, with little or no degradation because of the deficiency in one or more proteases. Doubly and triply protease deficient mutants of *Escherichia coli* have been deposited with ATCC (accession numbers 55099, 55100 and 55101, respectively).

The response of *E. coli* to heat shock is characterized by the rapid transient induction of a specific set of at least seventeen proteins (Neidhart and VanBogelen 1987). Transcription of the heat shock regulon is controlled by the RNA polymerase sigma factor, $\sigma^{32}$, encoded by the rpoH gene (Gross, et al. 1990, Helmann and Chamberlin 1988). rpoH is required for growth at temperatures greater than 20° C. (Zhu, et al. 1988). Several heat shock proteins (hsps) are involved in the in vivo stability of proteins (Gross, et al. 1990, Strauss, et al. 1988), and their overproduction results in enhanced rates of puromycyl fragment decay. In turn, the accumulation of abnormal polypeptides, resulting from treatment with puromycin, incorporation of canavanine or overproduction of foreign proteins, causes induction of the heat shock response (Baneyx and Georgiou, 1992). The degradation of abnormal cytoplasmic proteins is decreased by mutations in the rpoH gene which lead to lower expression of heat shock genes (Goff and Goldberg, 1984, 1985). This effect is at least in part due to a decrease in the synthesis of the cytoplasmic proteases Lon and Clp in rpoH mutants.

It is not known if rpoH mutations affect the expression of proteolytically sensitive secreted proteins. An increase in the stability of secreted proteins in strains carrying such mutations cannot be predicted since $\sigma^{32}$ the rpoH gene product is not known to affect the synthesis of any of the known secreted proteases.

Strains, Plasmids, Bacteriophages and Media

The bacterial strains and plasmids used are listed in Table 1. Bacteriophage T4 gene 2 mutant (N5 lam) was provided as a gift from E. Goldberg (Tufts Medical School, Dept. of Microbiology). Cultures were grown in LB medium (Difco) supplemented with 0.2% glucose and the appropriate concentrations of antibiotics. M9 medium was supplemented with 0.2% casein amino acid hydrolysate, 0.2% glucose and the appropriate antibiotics. W salts medium has been described (Smith, et al., 1971) and consists of 10.5 g $K_2HPO_4$, 4.5 g $KH_2PO_4$, 0.102 g $MgSO_4.7H_2O$ per liter of solution containing 0.2% L-glutamine, 0.2% glucose, and 0.2% $(NH_4)_2SO_4$. Ampicillin, tetracycline, kanamycin and chloramphenicol were added to the growth medium as required at 50 μg/ml, 25 μg/ml, 50 μg/ml and 20 μg/ml final concentration respectively.

Mutant *E. coli* deficient in one or more genes encoding a protease have been deposited with the American Type Culture Collection (ATCC), 12301 Parklawn Drive, Rockville, Md. 20852, USA. The bacteria are identified as *Escherichia coli* SF120 (ATCC 55099), *Escherichia coli* SF103 (ATCC 55100), and *Escherichia coli* (ATCC 55101) deficient respectively in ompT, degP and ptr genes (ATCC 55099), ptr gene (ATCC 55100), and ompT and degP genes (ATCC 55101). The deposits were made in accordance with the Budapest treaty.

TABLE 1

Bacterial strains and plasmids.

| Strain or plasmid | Genotype or characteristics | Source or reference |
|---|---|---|
| Strain | | |
| *E. coli* | | |
| D301 | RP487 recD1903 Δ(lacIZYA-ul69) | Russel et al., 1989 |
| JC7729 | K-12 recB21 sbcB15 his327 leu(am) trpE9829 lac str321 thi | |
| KS472 | F⁻ ΔlacX74 galE galK thi rpsL (strA) ΔPhoA(PvuII) | Strauch & Beckwith, 1988 |
| KS474 | KS272 degP41 (ΔPstI-Kan$^r$) | Strauch & Beckwith, 1988 |
| SF100 | KS272 ΔompT | Baneyx and Georgiou, 1990 |
| SF101 | D301 ptr32::ΩCat$^r$ | Baneyx and Georgiou, 1991 |
| SF103 | KS272 ptr32::ΩCat$^r$ | Baneyx and Georgiou, 1991 |
| SF110 | KS272 ΔompT degP41 (ΔPstI-Kan$^r$) | Baneyx and Georgiou, 1990 |
| SF112 | KS272 ΔompT ptr32::ΩCat$^r$ | Baneyx and Georgiou, 1991 |
| SF115 | KS272 ptr32::ΩCat$^r$ degP41(ΔPstI-Kan$^r$) | Baneyx and Georgiou, 1991 |
| SF120 | KS272 ptr32::ΩCat$^r$ degP41(ΔPstI-Kan$^r$) ΔompT | Baneyx and Georgiou, 1991 |
| SC122 | lac(Am)trp(Am)pho-(Am)supC(Ts)rpsL-(strA) mal(Am) | Straus et al., 1988 |
| CAG597 | SC122 rpoH165(Am)-Tn10 | Straus et al., 1988 |
| SF200 | SC122 degP41 (ΔPstI)::ΩKan$^r$ | |
| SF210 | CAG597 degP41 (ΔPstI)::ΩKan$^r$ | |
| MC4100 | F⁻ araD Δ(argF-lac) U169 rpsL relA flbB deoC ptsF rbsR | Ausubel, 1987 |
| BR3635 | MC4100 mini-Tn10 near rpoH⁺ | Tilly, 1991 |
| BR3637 | MC4100 mini-Tn10 near rpoH15 | Tilly, 1991 |
| SF300 | BR3635 degP41(ΔpstI)::ΩKan$^r$ | |
| SF310 | BR3637 degP41(ΔpstI)::ΩKan$^r$ | |
| Plasmid | | |
| pACYC184 | 4.2 kbp medium copy number plasmid; Cat$^r$ Tet$^r$ | Ausubel et al., 1987 |
| pCDK3 | pBR325 derivative carrying a 19 kbp BamH I fragment mapping (thyA argA). | Dykstra et el., 1984 |
| pCS1 | pUC19 derivative carrying a 3.2 kbp PvuI SpA-bla fragment from pFB3; Amp$^r$. | Baneyx and Georgiou, 1991 |
| pFB3 | 9.86 kbp pBR322 derivative carrying SpA-bla; Amp$^r$ Kan$^r$. | Baneyx and Georgiou, 1989 |
| pFB5 | pCS1 derivative carryng an 8 kbp Sal I fragment encoding ptr; Amp$^r$. | Baneyx and Georgiou, 1991 |
| pFB6 | pFB5 derivative (ptr32::ΩCat$^r$); Amp$^r$ Cat$^r$. | Baneyx and Georgiou, 1991 |

$^a$Abbreviations: Amp$^r$, ampicillin resistance; Cm$^r$, chloramphenicol resistance; Kan$^r$, kanamycin resistance; Tet$^r$, tetracycline resistance; SpA-Bla, *S. aureus* protein A-β-lactamase fusion protein.

Enzymes and Chemicals

Restriction and DNA modifying enzymes were purchased from Boehringer-Mannheim, New England Biolabs and Promega. All recombinant DNA procedures were performed according to Ausubel et al. (Ausubel, et al., 1987). Oxidized insulin B-chain and penicillin G were obtained from Sigma. All chemicals used were of biological grade.

Southern Blots

Southern blots were performed essentially as described by Ausubel et al. (Ausubel, et al., 1987). Genomic DNA was isolated as described (Ansubel, et al., 1987), separated in 0.8% agarose gels and transferred overnight to nitrocellulose (Schleicher & Schuell BA85). DNA was crosslinked to nitrocellulose by baking for 2 hr at 80° C. in a vacuum oven. Nonradioactive digoxigenin-11-dUTP probes were prepared using the Genius system (Boehringer Mannheim) according to the manufacturer's instructions.

Pulse-Chase Experiments

Cells were grown in labeling medium supplemented with 19 amino acids but no methionine (Georgiou, et al., 1988) to mid-exponential phase (OD=0.5 at 600 nm). 100 μCi of $^{35}$S-Met were added to the growth medium. After two to five minutes, 1 ml of 0.5 mg/ml cold methionine was added and a zero point taken immediately. At specified times after initiation of the chase, 1 ml samples were transferred to microfuge tubes kept on ice and containing 50 μl of 34 mg/ml chloramphenicol. The cells were centrifuged, washed with 1 ml of 10 mM Tris HCl, pH 8.0, resuspended in lysis buffer (10 mM Tris HCl, pH 8.0, 1% SDS, 1 mM EDTA) and boiled for 3 minutes. Immunoprecipitation was performed as described (Baneyx and Georgiou, 1990). Autoradiograms were scanned with a prototype digital Clayton video densitometer developed at the University of Texas by Larry Poulson.

Penicillinase and Insulin Degradation Assays 3 ml samples from cultures grown as specified were centrifuged at 8,000 x g for 8 min, the pellets were resuspended in 3 ml 50 mM potassium phosphate, pH 6.5 and disrupted by French pressing at 20,000 psi. The insoluble fraction was removed by centrifugation. Penicillinase activities were measured by spectrophotometry at 240 nm as previously described (Baneyx and Georgiou, 1989) using a 0.5 g/l penicillin G solution in 50 mM potassium phosphate, pH 6.5 as a substrate.

For insulin assays, cells were grown overnight in LB medium supplemented with 0.2% glucose and the appropriate concentrations of antibiotics as required. Osmotic tractions were collected by the method of Nossal and Heppel (Nossal and Heppel, 1966) and concentrated using Amicon Centricon-10 microconcentrators. 30 μg of periplasmic proteins were mixed with 100 mM ammonium bicarbonate buffer, pH 8.4, and exactly 250 μg of oxidized insulin B-chain was added. The final volume was 500 μl. Samples were incubated for 3.5 hr at 37° C. 20 μl aliquots (corresponding to an initial insulin concentration of 10 μg) were boiled in loading buffer to stop the reaction and loaded onto a 22% polyacrylamide gel. 10 μg of purified insulin was used as a control.

General Methods

SDS-PAGE was performed according to Laemmli (Laemmli, 1970) in 22% gels. Protein concentrations were determined with the BioRad protein assay using bovine serum albumin as a standard.

EXAMPLE 1

Construction of ptr Mutants

The overall strategy used to construct ptr mutants is shown in FIG. 1. Plasmid pCDK3 which carries a 19 kbp insert mapping the thyA-argA region of the *E. coli* genome was digested with Sal I and BamH I. The 8 kbp Sal I fragment containing the ptr gene, was isolated by low melting point agarose. This DNA fragment was ligated into the unique Sal I site of plasmid pCS1 to yield plasmid pFB5. Plasmid pCS1 was itself generated by transferring the protein A-β-lactamase gene into a plasmid vector having a different origin of replication (Baneyx and Georgiou, 1990). pFB5 contains a unique Cla I site, located approximately 1000 bp downstream from the start codon of the ptr gene. A functional chloramphenicol acetyl transferase (Cat) gene was obtained in a 1.7 kbp Hinc II-Xmn I fragment from plasmid PACYC184. Plasmid pFB5 was linearized with Cla I, treated with Klenow to generate blunt ends, and ligated to the 1.7 kbp DNA fragment from pACYC184. Competent cells were transformed with the ligation mixture. Transformants were selected on chloramphenicol plates and tested for ampicillin resistance. The structure of the resulting plasmid, pFB6, was confirmed by restriction analysis.

Plasmid pFB6 was digested with Sal I and the 9.7 kbp fragment was isolated. The chloramphenicol resistance insertional mutation in the ptr gene was transferred to the *E. coli* chromosome. *E. coli* strain D301 carries a tetracycline resistance insertional mutation in the recD gene that allows the cells to be transformed with linearized DNA (Russell, et al., 1989). Competent D301 cells were transformed with about 1.5 μg of the 9.7 kbp linearized DNA and plated on chloramphenicol plates. To ensure that no intact pFB6 had been cotransformed, the transformants were tested for ampicillin sensitivity. A chloramphenicol resistant ($Cat^r$), tetracycline resistant ($Tet^r$), ampicillin sensitive ($Amp^s$) colony, SF101, was selected. The ptr mutation was designated ptr32::$\Omega Cat^r$. Since SF101 is a D301 derivative, it also contains the tetracycline resistance insertional mutation in its recD gene. The ptr mutation was transferred into bacterial strain KS272 by generalized P1 transduction. Transductants containing the ptr32::$\Omega Cat^r$ mutation were isolated on the basis of chloramphenicol resistance. These colonies were further selected for tetracycline sensitivity to ensure that they did not contain the recD mutation present in D301. This process yielded an *E. coli* strain carrying a chloramphenicol resistance insertional mutation in the ptr gene as well as a functional recD gene, i.e. having an intact exonuclease V activity. The selected strain SF103 has been deposited with ATCC, Accession number 55100.

Figure 2:
FIG. 2 is a Southern blot analysis of genomic DNA digested with Hind II and Cla I. Lane 1, KS272 (wild type); lane 2, SF 103 (ptr); lane 3, SF115 (ptr degP); lane 4, SF120 (ptr degP ompT).

The correct insertion of the chloramphenicol cartridge was confirmed by Southern blotting (FIG. 2). A Hinc II-Xmn I chloramphenicol probe derived from plasmid pACYC184 and labeled with digoxigenin-11-dUTP hybridized with Hinc II+Cla I digested genomic DNA from SF103 (lane 2) but did not hybridize with DNA from the parental strain KS272.

Figure 3:
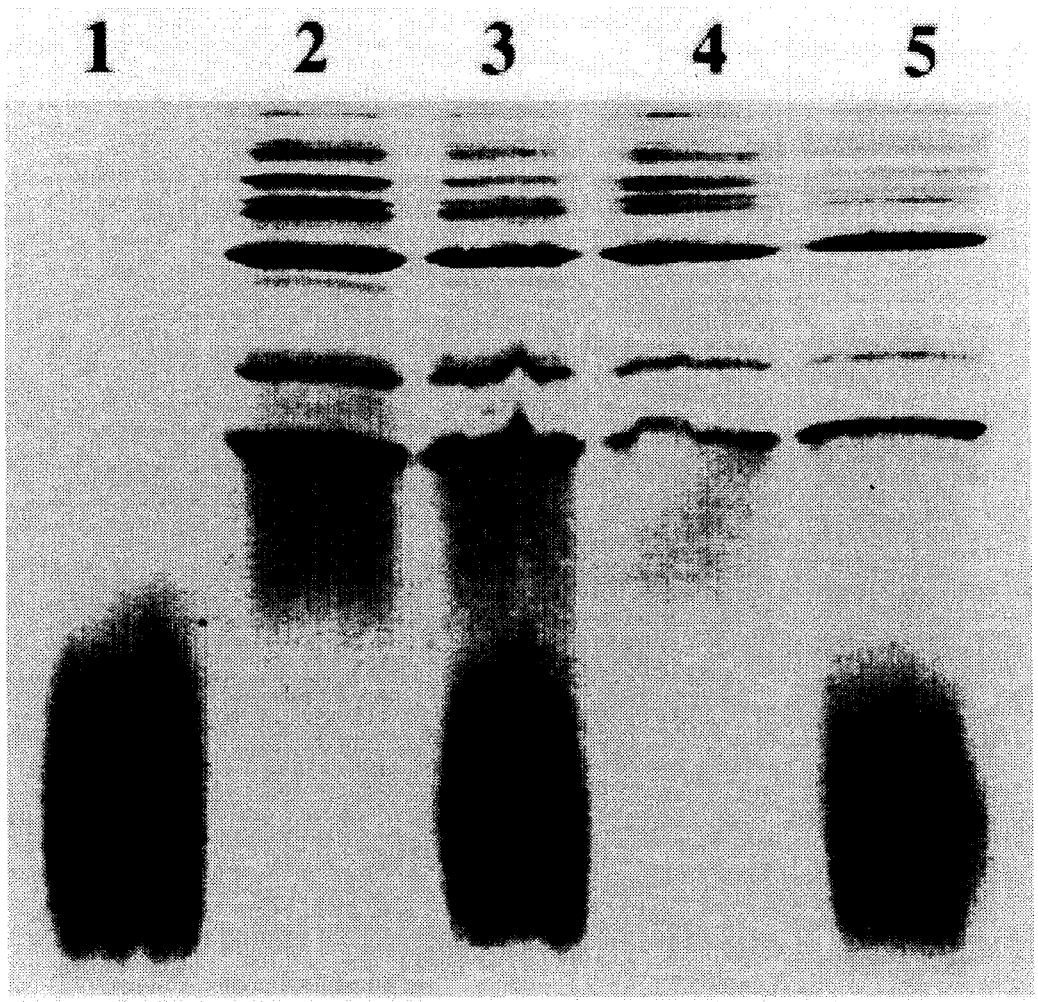
FIG. 3 shows the results of the insulin degradation assays. Lane 1, purified insulin control; lane 2, KS272 (wild type); lane 3, SF103 (ptr), lane 4, SF110 (ompT degP); lane 5, SF120 (ptr degP ompT).

Because Protease III is the only cell envelope protease which has been reported to rapidly degrade insulin, the absence of Protease III proteolytic activity in the ptr32::$\Omega Cat^r$ mutant SF103 was demonstrated as follows. Strains KS272 and SF103 were grown in LB medium supplemented with glucose and the appropriate antibiotics for 24 hours. The periplasmic traction of the cells was collected by the method of Nossal and Heppel (Nossal and Heppel, 1966) and concentrated by ultrafiltration. Periplasmic proteins were incubated with oxidized insulin B-chain and resolved by SDS-PAGE as described in Materials and Methods. FIG. 3 shows that no appreciable degradation was observed with SF103 (lane 3). In contrast, no intact insulin could be detected after incubation with the osmotic shock fractions of the isogenic strains KS272 (lane 2). Therefore, the ptr32::$\Omega Cat^r$ mutant SF103 does not possess the insulin degrading activity typical of strains containing an intact Protease III activity.

Finally, the presence of an intact exonuclease V activity in SF103 was demonstrated in the following manner. *E. coli* cells containing a defective exonuclease V enzyme (i.e., a mutation in one or more of the recB, recC and recD genes) are fully permissive for bacteriophage T4 gene 2 mutants (T4 $2^-$). However, T4 $2^-$ is unable to infect cells containing an intact exonuclease V activity. Strains JC7729, KS272 and SF103 were infected at different multiplicities of infection with T4 $2^-$(amN51) as described (Banex and Georgiou, 1991). Although T4 $2^-$ formed numerous plaques on the recB strain JC7729 (the titer of the phage was about $3\times10^9$ PFU/ml on JC7729), none were obtained on KS272 or SF103, indicating the presence of a fully functional exonuclease V in these strains. Furthermore, streaks of SF103 cells exposed to 1.1 mW of UV radiation per $cm^2$ for up to 100 seconds did not display the reduced viability typically observed in recB recC recD mutants. The ptr mutant SF103 grew to an optical density at 600 nm of about 1.8 in a variety of media (e.g., LB, M9, W salts).

EXAMPLE 2

Construction of ptr degP Mutants

P1 generalized transduction was used to transfer the ptr32::$\Omega Cat^r$ mutation from SF101 to a degP mutant KS474. Transductants were selected for chloramphenicol resistance and tetracycline sensitivity to confirm the presence of the ptr mutation and the absence of the recD mutation respectively. The resulting colonies were further tested for kanamycin resistance, indicating the presence of the degP mutation.

The resulting double protease-deficient strain, SF115, was tested for (i) proper insertion of the chloramphenicol resistance cartridge (FIG. 2, lane 3), (ii) absence of proteolytic activity against insulin, and (iii) presence of an intact exonuclease V activity, with a series of tests as described in Example 1.

EXAMPLE 3

Construction of ptr ompT Mutants

Mutants in both ptr and ompT were constructed in a manner analogous to that used for the construction of the ptr degP double mutant SF115, described in Example 3, except that P1 generalized transduction was used to transfer the ptr32::$\Omega Cat^r$ mutation from SF101 to SF100. The latter strain contains a deletion in the chromosome which includes the ompT gene (Baneyx and Georgiou, 1990). Transductants were selected for chloramphenicol resistance and tetracycline sensitivity to confirm the presence of the ptr mutation and the absence of the recD mutation, respectively.

The resulting double protease-deficient strain SF112, was tested for (i) proper insertion of the chloramphenicol resistance cartridge, (ii) absence of proteolytic activity against insulin, and (iii) presence of an intact exonuclease V activity, as described in Example 1.

EXAMPLE 4

Construction of ptr degP ompT Mutants

Generalized P1 transduction was used to transfer the ptr32::ΩCat$^r$ mutation from strain SF101 into a ompT degP stain. The ompT degP mutant was obtained as follows:

Two mutations were combined in a single strain using P1 transduction to transfer chromosomal DNA from ompT mutant, *Escherichia coli* strain UT4400, into a degP mutant strain KS474. Strain UT4400 is a spontaneous mutant in which the entire ompT gene together with a sizable piece of adjacent DNA has been deleted from the chromosome. Strain KS474 contains a gene that confers resistance to the antibiotic kanamycin at the position where the degP gene is normally located. Cells were selected for resistance to kanamycin and to colicin D (resistance to this compound is encoded by one of the genes deleted from ompT mutant strain UT4400). In addition, the absence of OmpT was tested by examining the outer membrane proteins by electrophoresis (Baneyx and Georgiou, 1990).

Following transduction of ptr32::Ωcat$^r$ from strain SF101 into the ompT degP strain, transductants were selected for chloramphenicol resistance and tetracycline sensitivity to confirm the presence of the ptr mutation and the absence of the recD mutation, respectively. The resulting colonies were further tested for kanamycin resistance, indicating the presence of the degP mutation. The selected triply protease-deficient mutant strain was designated SF120 (ATCC, Accession number 55099).

Strain SF120 was tested for (i) proper insertion of the chloramphenicol resistance cartridge (FIG. 2, lane 4), (ii) absence of proteolytic activity against insulin (FIG. 3, lane 5), and (iii) presence of an intact exonuclease V activity, with a series of tests as described in Example 1.

EXAMPLE 5

Expression of Protein A-β-Lactamase from Protease-Deficient Mutants

Figure 4:
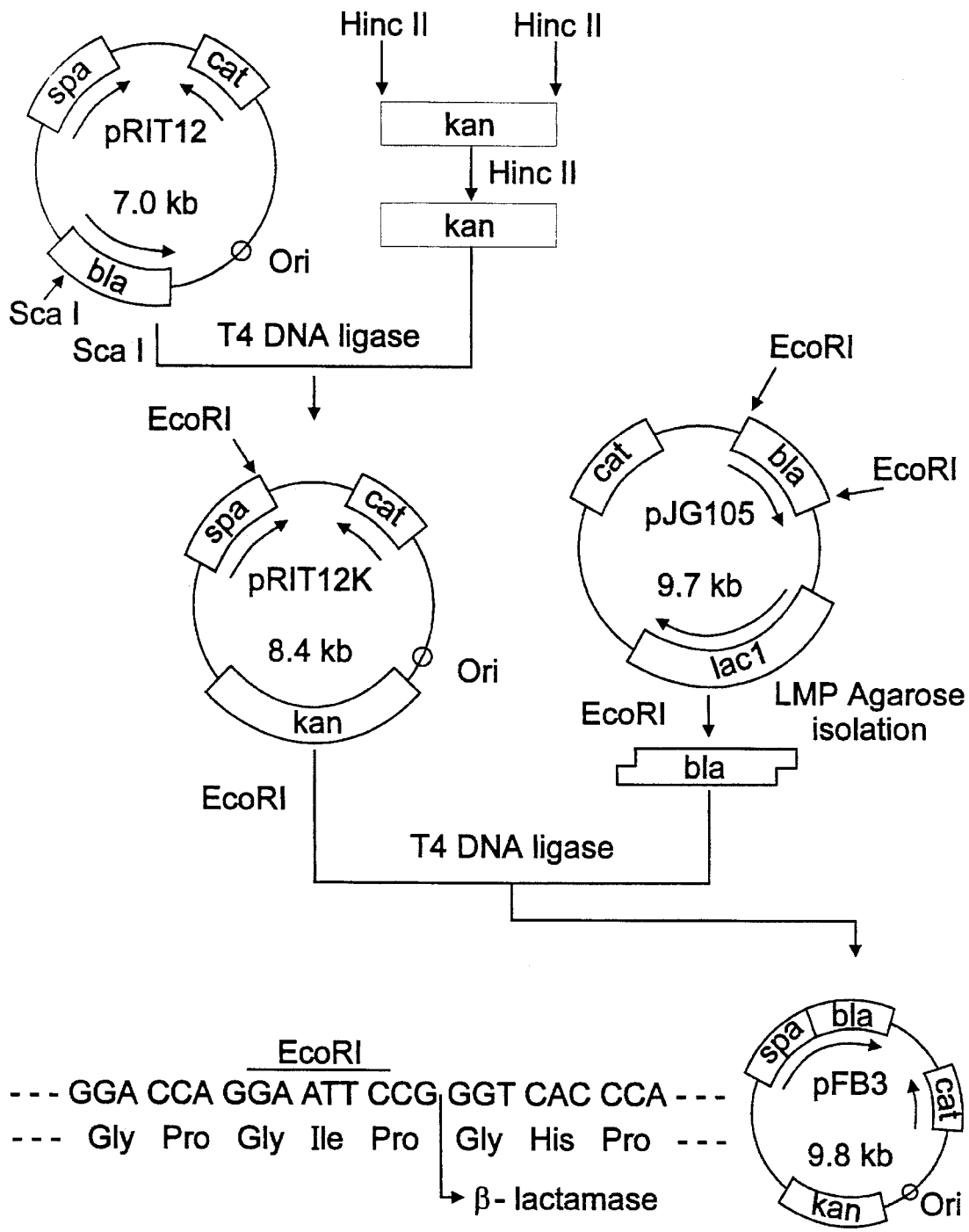
FIG. 4 shows the construction of plasmid vector pBF3, indicating restriction sites, localization of origins of replication, and the nucleotide sequence SEQ. ID NO:1 at the junction of protein A and mature β-lactamase gene. The amino acid sequence shown in the figure is designated herein as SEQ ID NO:2. Boxes show the relative position of genes coding for β-lactamase (bla), protein A (spa), chloramphenicol acetyl transferase (cat), tetracycline resistance (tet) and lac I.

Plasmid pFB3 encodes a hybrid protein constructed by in-frame fusion of the genes coding for *Staphylococcus aureus* protein A and the *E. coli* enzyme TEM β-lactamase (FIG. 4). β-lactamase is a small, monomeric enzyme involved in the hydrolysis of the β-lactam ring of many antibiotics such as penicillin, nitrocefin, and cephaloridine. β-lactamase activity against the substrate benzylpenicillin was determined using the spectrophotometric methods described in Materials and Methods.

Protein Expression in Protease Deficient Mutants

The protease-deficient mutants described in Examples 1 to 4 were shown to augment the expression of protein A-β-lactamase as follows: Strains were transformed with the plasmid vector pFB3. Cultures were grown for 24 hours in LB medium and the total penicillinase activity was assayed as described in Materials and Methods. Penicillinase specific activities of these strains are shown in Table 2.

TABLE 2

Influence of different protease-deficient mutant strains on the expression of protein A-β-lactamase from the plasmid vector pFB3

| Strain (plasmid) | Strain Characteristics | Growth medium | Total penicillinase specific activity (U/mg) ± SD | % increase |
|---|---|---|---|---|
| KS272(pFB3) | ompT$^+$ degP$^+$ ptr$^+$ | LB | 15.2 + 2.9 | — |
| KS474(pFB3) | ompT$^+$ degP ptr$^+$ | LB | 47.9 ± 8.3 | 215 |
| SF100(pFB3) | ompT degP$^+$ ptr$^+$ | LB | 28.2 ± 7.1 | 85 |
| SF103(pFB3) | ompT$^+$ degP$^+$ ptr | LB | 32.6 ± 12.5 | 115 |
| SF110(pFB3) | ompT degP ptr$^+$ | LB | 87.9 ± 17.2 | 478 |
| SF115(pFB3) | ompT$^+$ degP ptr | LB | 77.5 ± 16.5 | 410 |
| SF120(pFB3) | ompT degP ptr | LB | 86.9 ± 10.1 | 472 |

Table 2 indicates that a single mutation in the ptr gene (strain SF103) increased the expression of protein A-β-lactamase by about 2-fold compared to the parental strain KS272. This improvement is comparable to that observed with the single ompT mutant SF100 (lane 3). An approximate 3-fold increase in expression is obtained with the single degP mutant KS474. Use of the double mutants SF110 (ompT degP) and SF115 (ptr degP), described in Example 2, increases the expression of protein A-β-lactamase by more than 5-fold relative to the parental strain KS272. The triple mutant SF120 (ptr degP ompT) described in Example 4, also provided a 5 to 6-fold increase in protein A-β-lactamase expression.

Figure 5:
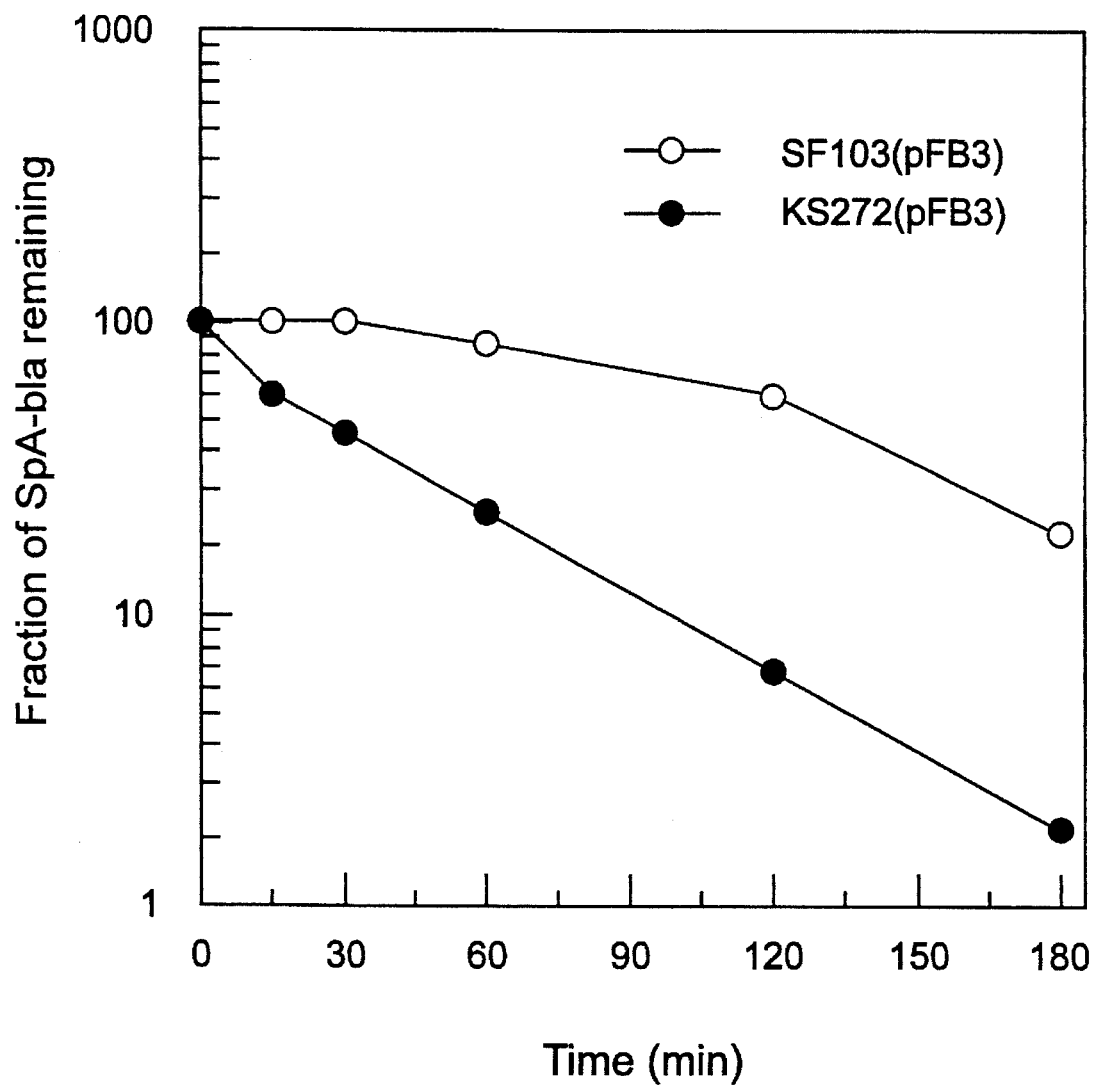
FIG. 5 shows the result of an analysis of the stability of protein A-β-lactamase in the wild type strain KS272 (solid circles) and the ptr mutant SF103 (open circles).

Enhanced expression levels of protein A-β-lactamase in the ompT degP double mutant SF110 were confirmed by radioactive pulse-chase experiments as described in Materials and Methods. FIG. 5 shows that the half-life of the fusion protein was approximately 30 min in the degP single mutant strain KS474, but was increased to about 100 minutes in the ompT degP double mutant strain SF110. Essentially no degradation of the fusion protein was evident in the double mutant for the first hour following the initiation of the chase, demonstrating that *E. coli* strains deficient in multiple proteases also provide enhanced levels of expression of protein A-β-lactamase in exponentially growing cells.

Similarly, no degradation of protein A-β-lactamase was observed in the ptr mutant SF103 for the first 30 minutes following the initiation of the chase.

Protein Expression in rpoH and rpoH/protease Deficient Mutants

The effect of rpoH mutations alone and in combination with mutations in cell envelope *E. coli* proteases on secreted proteins was examined. As discussed, it is known that certain heat shock proteins such as Lon and Clp are involved in the degradation of abnormal proteins. However, it was not known if rpoH affected the expression of proteolytically sensitive secreted proteins. Surprisingly, it was found that the expression of protein A-β-lactamase was enhanced in certain rpoH mutants compared with wild-type strains and even more surprisingly was significantly further enhanced in degP/rpoH double mutants.

RpoH15 is a missense mutation which affects the binding of σ$^{32}$ to the −35 region of heat shock promoters (Yura et al. 1984). The isogenic strains BR3635 and BR3637 (rpoH15) were transformed with pFB3, the plasmid containing the gene for the protein A-β-lactamase fusion, and grown at 30° C. in LB medium. Cells carrying the rpoH15 mutation exhibited 20-fold higher β-lactamase activities compared to the isogenic control as shown in Table 3.

TABLE 3

Total β-lactamase specific activites of bacterial strains harboring pFB3[a]

| Strain (plasmid) | Relevant genotype | Lysate β-lactamase activity (U/mg) ± SD[b] |
|---|---|---|
| BR3635(pFB3) | wild type | 0.37 ± 0.21 |
| BR3637(pFB3) | rpoH15 | 7.32 ± 1.46 |
| SF300(pFB3) | degP | 2.88 ± 0.58 |
| SF310(pFB3) | degP rpoH15 | 33.2 ± 1.49 |
| SC122(pFB3) | wild type | 0.76 ± 0.09 |
| CAG597(pFB3) | rpoH165 | 2.70 ± 1.25 |
| SF200(pFB3) | degP | 2.56 ± 0.47 |
| SF210(pFB3) | degP rpoH165 | 33.3 ± 4.9 |

[a]Cells were grown at 30° C. for 24 hrs in LB medium supplemented with 0.2% glucose and 50 μg/ml of both ampicillin and kanamycin.
[b]The lysate activity is defined as the ratio of β-lactamase activity to total protein concentration. The standard deviation (SD) is also expressed in units per milligram.

The effect of the rpoH15 allele on the expression of the fusion protein is enhanced in strains that are deficient in the major cell envelope protease DegP. Strains SF300 and SF310 were constructed by P1 transduction of a partial deletion in the degP gene linked to a Kan[r] marker (Strauch et al., 1989) into BR3635 and BR3637 as previously discussed. Strain SF310 grew at 37° C. but not at 42° C. as expected, due to the presence of the rpoH15 allele. The expression of the protein A-β-lactamase fusion in the two strains was determined as described. The β-lactamase activity of the fusion protein was almost 100-fold higher in the rpoH15 degP41 mutant compared to the parental strain, as indicated in Table 3.

The degP mutation was transferred into strain CAG597 which has the rpoH165 amber mutation and a temperature sensitive suppressor that allows growth at 37° C. but not at 42° C. Strain SF210 (rpoH15 degP) exhibited reduced levels of heat shock proteins when grown at 30° C. At 30° C., CAG597(pFB3) cells exhibited three-fold higher levels of the fusion protein compared to the rpoH[+] control, see Table 6. In strain SF210(pFB3) the β-lactamase activity was 10 times higher relative to either single mutant and about 50-fold higher compared to the wild type. Growth in rich media at 37° C. was poor and was accompanied by substantial cell lysis. Nevertheless, even under these conditions SF210 exhibited 36-fold and 14-fold higher activities than the wild type strain and the single degP mutant respectively.

EXAMPLE 6

In this example, mutants of *E. coli* were constructed from a combination of a chromosomal deletional mutation with selected missense mutations of the rpoH gene. A remarkable and unexpected enhancement of recombinant polypeptide expression was obtained compared with expression in a rpoH/degP double mutant compared to either rpoH15 mutant or degP mutant strains.

Construction of rpoH and rpoH/DegP Mutants ropH deletion mutants grow very poorly and became non-viable at temperatures above 20° C. (Zhu et al. 1990). For this reason, two well characterized rpoH alleles which resulted in reduced $\sigma^{32}$ activity and allowed growth at near physiological temperatures were used. These two alleles are designated rpoH15 and rpoH165. Both mutations reduce the level of the rpoH polypeptide product ($\sigma^{32}$) at the permissive temperature 30° C. At the restrictive temperature (42° C.) synthesis of $\sigma^{32}$ in rpoH15 or rpoH165 mutants is completely impaired and therefore the cells are not viable.

P1 transduction was used to transfer the degP41 mutation into BR3635, BR3637, SC122, and CAG597, generating strains SF300, SF310, SF200, and SF210, respectively. This generated two sets of isogenic strains. SF200 and SF300 carry a deletion mutation on the degP gene whereas SF210 and SF310 are rpoH15/degP and rpoH165/degP, respectively. SF310 and SF210 carrying conditional mutations in rpoH. Colonies that arose at 30° C. were scored for kanamycin (and in the case of SF310 and SF210, tetracycline) resistance and sensitivity for growth at 42° C. Strains SF310 and SF210 that carry the rpoH mutation cannot grow at 42° C. whereas strains that do not carry this mutation grow normally. All strains grew well in rich and minimal media at 30° C. The cells were transformed with plasmid pFB3, encoding the protein A-β-lactamase fusion and ampicillin resistant colonies. Cultures were grown in LB medium (Difco) supplemented with 0.2% glucose and the appropriate antibiotics. M9 medium (Georgiou, 1988)(1) was supplemented with 0.2% casein amino acid hydrolysate, 0.2% glucose, 10 μg/ml thiamine, and the desired antibiotics. Ampicillin, tetracycline, kanamycin, and chloramphenicol were added to the growth medium as required at 50, 25, 50, and 50 μg/ml (final concentrations), respectively.

EXAMPLE 7

The following example illustrates polypeptide expression in the triply protease deficient *E. coli* SF120 (ATCC Accession No. 55099). The proteolytically sensitive protein expressed was single chain antibody against *Chlamydia sp.* lipopolysaccharides. Remarkably, little or no degradation of the isolated scF$_v$ antibody was observed. By contrast, the use of other expression systems resulted in only minute, impractical expression levels.

Expression of scF$_v$ Antibody in Triply Protease Deficient *E. coli* cDNA for single chain antibody against *Chlamydia sp.* lipopolysaccharides was fused to the C-terminus of the Maltose Binding Protein (MalE) using pMAL-p2 (New England Biolabs, MA). A sequence encoding for a dodecapeptide from Herpes Simplex Virus (HSV) was fused to the C-terminus of MalE-scF$_v$, thereby flanking both the C-terminus and N-terminus to known sequences to which antibodies are available. This enabled detection of proteins containing an intact C-terminus by Western blotting using anti-HSV antibodies.

The pMAL-p20scF$_v$-HSV vector encoding the protein fusion was transformed into a variety of commonly used laboratory strains. Cells were grown in shake flasks in LB media at 37° C. and induced when the cells reached mid-exponential phase (optical density at 600 nm between 0.3–0.4). Cultures were harvested one hour after induction and samples were boiled in electrophoresis loading buffer. The level of protein expression was monitored by Western blotting using the anti-HSV antibodies. Anti-HSV antibody recognized the pMA1-p2-scF$_v$-HSV fusion.

The band corresponding to the intact pMAL-scFv-HSV fusion was substantially stronger in the triple mutant SF120 compared to the wild type strains. Also appreciable stabilization was observed in the double mutant SF115. The production of higher levels of the intact fusion protein was accompanied by a reduction in the level of proteolytic degradation products that could be detected in the Western blot.

In contrast, expression of the protein in SF120 cells grown under identical conditions clearly showed no degradation products. Only a single band of the correct molecular weight was detected on the Western. As a consequence of the absence of degradation products, yields were significantly increased and subsequent purification of scF$_v$ to homogeneity was greatly simplified.

EXAMPLE 8

The following example describes the construction of a triply protease deficient/rpoH 15 mutant *E. coli*.
degP, ptr, ompT, rpoH15 *E. coli*

P1 transduction was used to transfer the rpoH15 mutation from strain BR3637 into the triply protease deficient strain SF130 (degP41(ΔPstI)::ΩKan$^r$, ptr, ompT). The rpoH15 mutation in strain BR3637 is linked to a mini Tn-10 transposon conferring resistance to the antibiotic tetracycline. Consequently, transductants of SF130 could be selected on plates containing 25 μg/m of tetracycline. TetR colonies were subsequently screened for inability to grow at 42° C., the restrictive temperature for rpoH mutants. One tetracycline resistant, temperature-sensitive colony was selected for further studies. This strain was designated SF130. Strain SF130 has the genotype: KS272 degP41 (ΔPstI)::ΩKan$^r$, ptr, ompT, rpoH15 near mini TN10. Strain SF130 grew well at 30° C. in LB broth supplemented with 0.2% w/v casein amino acids and 0.2% w/v glucose. At that temperature the growth rate of SF130 was almost identical to the parental strain SF120 which does not contain the rpoH15 mutation. However, when grown at 37° C., SF130 grew very poorly as expected due to the rpoH15 mutation. Growth at that temperature also resulted in a high frequency of reversion to the ability to grow at 42° C.

SF130 cells were transformed with plasmid pFB3. Transformants were selected for resistance to ampicillin. One transformant colony was subsequently used for further studies. The cells were grown in liquid culture and the β-lactamase activity was determined as described in example 7. When the triply protease deficient mutant SF120 transformed with pFB3 was grown under these conditions, the express of protein A-β-lactamase as determined by the activity of β-lactamase, was 86.9±20 U/mg total cell protein. Surprisingly, SF130/pFB3 cells exhibited 30–50% lower β-lactamase activities compared to the rpoH$^+$ parental strain SF120. Thus while rpoH mutations exert a beneficial effect on the expression of proteolytically susceptible proteins in some genetic backgrounds in other backgrounds, particularly in strains that are already impaired in the synthesis of several proteases, rpoH mutations can be detrimental for protein expression.

EXAMPLE 9

P1 transduction was used to transfer a prc(tsp) deletion mutation from strain KS1000 [Δprc(tsp)::kan1] (Silber et al. 1991) to strains KS272, SF100, SF103 to give strains HM100, HM110 and HM113, respectively. Transductants were selected on plates with kanamycin and the absence of a functional prc(tsp) gene was confirmed by: (1) inability to grow on LB plates with no salt upon incubation at 42° C., a phenotype conferred by Δprc(tsp) and (2) the lack of a Prc(Tsp) band on western blots probed with polyclonal antisera specific for Prc(Tsp). In addition, a quadruple mutant deficient in DegP, OmpT, Ptr and Tsp was constructed as follows. A prc mutation that eliminates the production of functional protein was transferred from strain JE7921 [K27 prc-7304, eda-51::Tn10] (Hara et al. 1991) to the triple mutant strain SF120 by P1 transduction. The eda locus is linked to the prc(tsp) mutation and thus transductants could be selected by plating on tetracycline containing plates. Tetracycline resistant colonies were characterized further for absence of the Prc(Tsp) protein by Western blotting as above. One colony was selected for further studies and designated HM130.

Strains KS272, HM100, HM110, HM113 and HM130 were transformed with plasmid PFB3 and the expression of Protein A-β-lactamase was tested as described in Example 5. The β-lactamase activity in different strains is shown below:

TABLE 4

| STRAIN | RELEVANT GENOTYPE | TOTAL ACTIVITY RELATIVE TO PARENTAL STRAIN (U/ml CULTURE) |
|---|---|---|
| KS272 | wild type | 100 |
| HM100 | prc(tsp) | 389 |
| HM110 | prc(tsp), ompT | 160 |
| HM113 | prc(tsp, ptr | 150 |
| HM130 | prc(tsp), ptr, degP, ompT | 480 |

From these results it can be seen that among the protease deficient mutants deficient in Prc(Tsp) the highest increase in the expression of the model secreted recombinant protein was obtained in the quadruple mutant HM130. The two double mutants, in contrast, exhibited lower levels of expression than the single mutant and substantially lower levels than the quadruple mutant.

EXAMPLE 10

Construction of a bacterium deficient in five proteases is contemplated to be within the scope of the invention, based on the novel double and triply protease microorganisms described in previous examples. Preparation of this construct is illustrated in the following example.
Construction of ptr ompT degP tsp(pre) Protease VI Mutants Construction of mutant organisms will involve the following steps: (i) cloning and amplification of a gene or part of a gene of a protease; (ii) mutagenesis of the isolated gene sequence to allow easy selection of the mutants; (iii) recombination of the mutated gene sequence into the chromosome; and (iv) transfer of the mutation into a strain deficient in three proteases.

Protease VI is isolated and purified from *Escherichia coli* using well known techniques (Swamy and Goldberg, 1982; Palmer and St. John, 1987; Pacaud, 1982). The amino terminal sequence of the purified protein is determined by gas phase sequencing. Degenerate oligonucleotide primers corresponding to the sequence of the first six or seven N-terminal amino acids are prepared by automated solid phase synthesis (Ausubel, et al. 1987). In separate experiments *E. coli* is mutagenized by transposon mitogenesis; strains containing a transposon linked to the protease VI gene are related. By linking the gene to a transposon, e.g. Tn10, whose sequence is known it is now possible to synthesize a second oligonucleotide primer (complementary to the transposon sequence). Having two primers available now enables PCR amplification to be performed. Amplification is carried out by polymerase chain reaction (PCR) using an additional primer which corresponds to a plasmid sequence. The amplified DNA is isolated and subcloned within a suitable vector containing appropriate restriction sites. The gene or part of the gene thus amplified is then used to screen an ordered plasmid *E. coli* library so that the gene is identified in the physical map of the genome, subsequently allowing the entire gene to be cloned. Once the protease gene has been cloned on a plasmid, mutations are generated in vitro as described in Example 1. A mutation resulting in deletion of a substantial fraction of the gene's DNA and linked to the antibiotic resistance gene is then isolated. The mutation is then transferred into the triple mutant strain SF120 to generate a quadruple mutant strain exhibiting substantial reduction in four protease activities. Strains in which the transposon has been excised are isolated by screening for cells that have lost the selectable marker. These cells will not exhibit tetracycline resistance but will be defective in Protease VI as well as OmpT, DegP and Protease III.

While the methods and compositions of this invention have been described in terms of preferred embodiments, it will be apparent to those of skill in the art that variations may be applied to the methods or compositions and in the steps or sequence of steps of the methods described herein without departing from the concept, spirit and scope of the invention. More specifically, it will be apparent that the methods may be practiced with variations of the genetically engineered bacteria herein described, whether by genetic engineering or by identification of the appropriate spontaneous mutants. All such similar substitutes and modifications apparent to those skilled in the art are deemed to be within the spirit, scope and concept of the invention as defined by the appended claims.

REFERENCES

The references listed below are incorporated herein by reference to the extent they supplement, explain, provide a background for or teach methodology, techniques and/or compositions employed therein.

Ausubel, F. M., Brent, R., Kingston, R. E., Moore, D. D., Seidman, J. G., Smith, J. A. and Struhl, K. in Current Protocols in Molecular Biology, John Wiley & Sons, New York, N.Y. (1987).

Baker, T. A., Grossman, A. D., and Gross, C. A. 1984. Proc. Natl. Acad. Sci. USA 81:6779–6783.

Baneyx, F. and Georgiou, G., Enzyme Microb. Technol. 11, 559–567 (1989).

Baneyx, F. and Georgiou, G., J. Bacteriol. 172, 491–494 (1990).

Baneyx, F. and Georgiou, G., J. Bacteriol. 173:2696–2703 (1991).

Baneyx, F. and Georgiou, G., in Stability of Protein Pharmaceuticals: Chemical and Physical Pathways of Protein Degradation, T. Akers and C. Manning (Eds), (1992).

Beckwith, J. R. and Strauch, K. L., WO 88/05821, Aug. 11, 1988.

Chang, A. C. Y. and Cohen, S. N., J. Bacteriol. 134, 1141–1156 (1978).

Chaudhury, A. and Smith G. R., J. Bacteriol. 160, 788–791 (1984).

Cheng, Y. S. E. and Zipser, D., J. Biol. Chem. 254, 4698–4706 (1979).

Dykstra, C. C., Prasher, D. and Kushner, S. R., J. Bacteriol. 157, 21–27 (1984).

Elish, M. E., Pierce, J. R. and Earhart, C. F., J. Gen. Microbiol. 134, 1355–1364 (1988).

Field, H., Rees, A. R., Yarranton, G. T., WO 89/02465, Mar. 23, 1989.

Georgiou, G., AIChE. J. 34, 1233–1248 (1988).

Georgiou, G., Shuler, M. L. and Wilson, D. B., Biotechnol. Bioeng. 32, 741–748 (1988).

Ghrayel, T. and Inouye, M., J. Biol. Chem. 259:463–467 (1984).

Goff, S. A., Casson, L. P., and Goldberg, A. L., Proc. Natl. Acad. Sci. USA 81:6647–6651 (1984).

Goff, S. A. and Goldberg, A. L., Cell 41:587–595 (1985).

Goldberg, A. L. and St. John, A. C., Ann. Rev. Biochem. 45, 747–803 (1976).

Gross, C. A., Straus, D. B., Erickson, J. W., and Yura, T. 1990. In R. Morimoto, A. Tissieres, and C. Georgopoulos (ed.), Stress proteins in biology and medicine. Cold Spring Harbor Laboratory, Cold Spring Harbor, N.Y.

Hara, H., Yamamoto, Y., Higashitani, A., Suzuki, H., and Nishimura, Y., J. Bacteriol. 173:4799–4813 (1991).

Helmann, J. D. and Chamberlin, M. J., Ann. Rev. Biochem. 57:839–872 (1988).

Hershko, A. and Ciechanover, A., Ann. Rev. Biochem. 51, 335364 (1982).

Huse, W. D., Lakshmi, S., Iverson, S. A., Kang, A. S., Alting-Mees, M., Burton, D. R., Benkovic, S. J. and Lerner, R. A., Science 246, 1275–1280 (1989).

Johnson, K., Charles, I., Dougan, G., Pickard, D., O'Gaora, P., Costa, G., Ali, T., Miller, I., Hormaecke, C., Mol. Micvrobiol. 5:501–407 (1991).

Laemmli, U. K., Nature (London) 227, 680–685 (1970).

Lazdunski, A. M., FEMS Microbiol. Rev. 63, 265–276 (1989).

Lundrigan, M. D. and Webb, R. M., FENS Microbiol. Lettr 97:51–56 (1992)

Maniatis, T., Fritsch, E. F. and Sambrook, J. in Molecular Cloning: A Laboratory Manual, Cold Spring Harbor, N.Y., Cold Spring Harbor Laboratory Press, 1982.

McIntosh, M. A., Chenault, S. S. and Earhart, C. F., J. Bacteriol. 137, 653–657 (1979).

Miller, C. G. in *Escherichia coli* and *Salmonella typhimurium*: Cellular and Molecular Biology, Vol. 1, F. C. Neidhardt, Ed., American Society for Microbiology, Washington, D.C., pp 680–691, 1987.

Nossal, N. G. and Heppel, L. A., J. Biol. Chem. 241, 3055–3062 (1966).

Pacaud, M., J. Biol. Chem. 257, 4333–4339 (1982).

Palmer, S. M. and St. John, A. C., J. Bacteriol. 169, 1474–1479 (1987).

Russell, C. B., Thaler, D. S. and Dahlquist, F. W., J. Bacteriol. 171, 2609–2613 (1989).

Silber, K. R., Keiler, K. C., and Sauer, R. T., Proc. Natl. Acad. Sci. U.S.A. 89:295–299 (1992).

Smith, G. R., Halpern, Y. S. and Magasanik, J. Biol. Chem. 246, 3320–3329 (1971).

Sodeinde, O. A. and Goguen, J. D., Infect. Immun. 57:1517–1523 (1989).

Strauch, K. and Beckwith, J., Proc. Natl. Acad. Sci. U.S.A. 85, 1576–1580 (1988).

Strauch, K. L., Johnson, K. and Beckwith, J., J. Bacteriol. 171, 2689–2696 (1989).

Straus, D. B., Walter, W. A., and Gross, C. A., Genes Dev. 2:1851–1858 (1988).

Swamy, S. K. H. and Goldberg, A. L., J. Bacteriol. 149, 1027–1033 (1982).

Tilly, K., J. Bacteriol. 173:6639–6642 (1991).

Yura, T., Tobe, T., Ito, K., and Osawa, T., Proc. Natl. Acad. Sci. USA 81:6803–6808 (1984).

Zhou, Y.-N., Kusukawa, Erickson, J. W., Gross, C. A., and Yura, T., J. Bacteriol. 170:3640–3649 (1988).

What is claimed is:

1. A recombinant *E. coli* or Salmonella deficient in chromosomal degP encoding protease DegP and harboring a mutationally altered rpoH gene conferring inability to induce a heat shock response.

2. A recombinant *E. coli* or Salmonella deficient in chromosomal genes degP, ompT and ptr encoding protease DegP, OmpT and Protease III and harboring a mutationally altered rpoH gene conferring inability to induce a heat shock response.

3. The recombinant *E. coli* or Salmonella of claim 1 or claim 2 wherein the rpoH gene is rpoH15.

4. The recombinant *E. coli* or Salmonella of claim 1 or claim 2 wherein the rpoH gene is rpoH165.

5. The recombinant *E. coli* or Salmonella of claim 2 further comprising a chromosomally deficient prc gene encoding Prc.

6. The recombinant *E. coli* or Salmonella bacterium of claim 5 wherein the rpoH gene is rpoH15 or rpoH165.

7. A recombinant *E. coli* or Salmonella bacterium deficient in chromosomal degP, ompT, ptr and prc encoding protease DegP, OmpT, Protease III and Prc respectively.

* * * * *